US008577444B2

(12) United States Patent
Klingenbeck-Regn et al.

(10) Patent No.: US 8,577,444 B2
(45) Date of Patent: Nov. 5, 2013

(54) METHOD AND DEVICE FOR MAKING CORRECTION INFORMATION AVAILABLE

(75) Inventors: Klaus Klingenbeck-Regn, Nürnberg (DE); Marcus Pfister, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 1146 days.

(21) Appl. No.: 12/075,738

(22) Filed: Mar. 13, 2008

(65) Prior Publication Data

US 2008/0234575 A1    Sep. 25, 2008

(30) Foreign Application Priority Data

Mar. 20, 2007    (DE) .......................... 10 2007 013 407

(51) Int. Cl.
*A61B 5/05* (2006.01)
*A61B 19/00* (2006.01)

(52) U.S. Cl.
USPC ............ 600/424; 600/427; 600/429; 606/130

(58) Field of Classification Search
USPC .................. 600/431, 424, 426, 407; 606/130
See application file for complete search history.

(56) References Cited

U.S. PATENT DOCUMENTS

| | | | | |
|---|---|---|---|---|
| 5,638,819 | A * | 6/1997 | Manwaring et al. | 600/424 |
| 6,006,127 | A * | 12/1999 | Van Der Brug et al. | 600/427 |
| 6,028,912 | A * | 2/2000 | Navab | 378/62 |
| 6,487,431 | B1 * | 11/2002 | Iwano et al. | 600/407 |
| 6,920,347 | B2 * | 7/2005 | Simon et al. | 600/424 |
| 7,346,385 | B2 * | 3/2008 | Bascle et al. | 600/424 |
| 2004/0078045 | A1 * | 4/2004 | Bascle et al. | 606/130 |
| 2004/0087852 | A1 * | 5/2004 | Chen et al. | 600/407 |
| 2004/0096091 | A1 | 5/2004 | Bascle et al. | |
| 2006/0041181 | A1 * | 2/2006 | Viswanathan et al. | 600/11 |

FOREIGN PATENT DOCUMENTS

| | | |
|---|---|---|
| DE | 10210646 A1 | 10/2003 |
| DE | 102005012985 A1 | 7/2006 |
| EP | 1323380 B1 | 7/2003 |
| WO | WO 03091839 A2 | 11/2003 |

OTHER PUBLICATIONS

CAS innovations AG, Precision in Therapy Planning and Navigation CAPPA Navigation System, http://www.cas-innovations.de/cms/index.php?id=6&L=1, 2006.
Graeme Patrick Penney, "Registration of Tomographic Images to X-ray Projections for Use in Image Guided Interventions", A thesis for the degree of Doctor of Philosophy of the University of London, Computational Imaging Science Group, Division of Radiological Sciences and Medical Engineering, Guy's, King's and St. Thomas' School of Medicine, King's College London, 1999, pp. 1-203.

* cited by examiner

*Primary Examiner* — Tse Chen
*Assistant Examiner* — Patricia Park (57) ABSTRACT

The invention relates to a method and a device for making correction information for correcting a guidance direction of an instrument. Based on a current position of the tip of the instrument and the current guidance direction of the instrument and the position of a target point in an object, a first straight line indicating the current guidance direction and a second straight line defined by the tip of the instrument and the target point in the object are determined. The second straight line intersects the first straight line and indicates the desired guidance direction. Based on the position of the first and second straight lines relative to one another, a digital item of correction information is specified, wherein the correction image has a correction diagram located in a plane in the perspective of the current guidance direction of the instrument.

11 Claims, 5 Drawing Sheets

METHOD AND DEVICE FOR MAKING CORRECTION INFORMATION AVAILABLE

CROSS REFERENCE TO RELATED APPLICATIONS

This application claims priority of German application No. 10 2007 013 407.1 filed Mar. 20, 2007, which is incorporated by reference herein in its entirety.

FIELD OF THE INVENTION

The invention relates to a method and a device for making correction information available for correcting a guidance direction of an instrument when said instrument is being guided in an object with the intention of guiding said instrument from a starting point on the object to a target point in the object.

BACKGROUND OF THE INVENTION

In some areas of technology it is necessary to guide an instrument to a target point in an object, and it is then no longer possible to observe at least the tip and part of the instrument visually once the instrument has been at least partly introduced into the object, so that some uncertainty remains as to where the instrument, in particular the tip of the instrument, is currently located within the object, and whether the current guidance direction of the instrument corresponds to the desired guidance direction of the instrument relative to the target point that the instrument was intended to reach within the object.

Such a problem area also exists in medical technology, for example in the case of punctures such as transdermal bile duct aspirations or biopsies, during which a needle is guided to a target tissue, as a rule using transillumination images, otherwise known as fluoroscopy. By using transillumination images projected from different directions, a doctor can check the position and orientation of the needle relative to the target area and guide the needle to the target area or target tissue in a patient's body. However, pinpoint guidance of the needle sometimes turns out to be challenging, since the only images that the doctor has at his disposal for checking and guiding the needle have been projected from different directions, and frequently the puncture target can be made out only indistinctly or not at all.

It has therefore been suggested that for better understanding of a patient's anatomy and the puncture target, a data set of preoperative 3D images of the puncture area should be recorded and the intraoperative transillumination images should then be registered with the 3D image data set. It then becomes possible to superimpose image data from the 3D image data set upon image data from the transillumination images, so that for example the puncture tissue or the puncture target can be displayed in the transillumination images for better control of the puncture.

Yet even when transillumination images are superimposed with image data from a preoperative 3D image, as is possible by performing a 2D-3D registration, uncertainties still remain in the course of the puncture. A transillumination image enhanced by 3D image data does in fact make the target tissue and the needle visible at the same time, but the exact position of the target tissue and the needle relative to one another is shown to only a limited extent, since as a rule the 2D transillumination image lacks not only target and separation information, but above all depth information.

Document DE 10 2005 012 985 A1 discloses a method for checking the guidance of a needle during a surgical operation on a patient; in this method a 3D image is provided showing at least the tissue area in which the operation is being carried out. A user of the system marks up the 3D image with the position of the starting point and at least the target point of the operation. A guidance path for the instrument to follow in space is automatically computed on the basis of these marks. The computed guidance path is projected and graphically displayed in transillumination tissue area images obtained intraoperatively, said guidance path taking account of the projection geometries of the transillumination images concerned. Information about how the direction of the needle needs to be corrected can also be displayed in such a transillumination image. In order to execute the method disclosed in document DE 10 2005 012 985 A1, the 3D image and the 2D transillumination images are registered with one another, as described for example in document DE 102 10 646 A1.

SUMMARY OF THE INVENTION

The object of the invention is to specify a method and a device of the type described in the introduction, in a way that simplifies correcting the guidance direction of an instrument.

According to the invention, this object is achieved by a method and a device for making correction information available for correcting a guidance direction of an instrument when said instrument is being guided to a target point, it being possible, based on a current position of the tip of the instrument, on the current guidance direction of the instrument and on the position of the target point in the object, to determine a first straight line in space indicating the current guidance direction of the instrument, and a second straight line in space defined by the tip of the instrument and the target point in the object, said second straight line intersecting the first straight line and indicating the desired guidance direction, it then being possible, based on the position of the first and second straight lines relative to one another in at least one correction image, to specify at least one digital item of correction information for correcting the current guidance direction of the instrument, wherein the correction image has a correction diagram located in a plane in the perspective of the current guidance direction of the instrument. Inventively, for the purpose of guiding the instrument, a system user is thus physically provided with a digital item of correction information in a correction image, which can also include information on the direction required for correction, in order to simplify the instrument user's task of correcting the current guidance direction of the instrument to the desired guidance direction.

With regard to the correction diagram, the current guidance direction of the instrument is perpendicular to the plane of the correction diagram. Thus, regarding the instrument correction required according to the item or items of information in the correction diagram, the user must actually or conceptually assume a position behind the instrument in order to correct the instrument's guidance direction on the basis of the item or items of digital correction information in the correction diagram. The correction diagram is therefore provided with a type of virtual or imaginary adjustment diagram arranged at the end of the instrument, amounting to a kind of joystick.

In one variant of the invention, the digital correction information takes the form of a correction angle which is referenced to the tip of the instrument, and through which the user must rotate the instrument in order to change from its current guidance direction to the required guidance direction. Since the positions of the first and second straight lines in space are known, the correction angle or angles between the straight lines can be computed by reference to various spatial coordinate systems.

According to an embodiment of the invention, the correction image provided to the user has a representation of the instrument and displays at least the course of the second straight line and preferably also the first straight line, which corresponds at least for the most part with the representation of the instrument.

According to another embodiment of the invention, the correction image is a projection image of the object or a projection image of the object having 3D image data, meaning that image data of the projection image and image data originating from a 3D image data set or volume data set generated from the object are merged with or superimposed on one another. In the medical field the projection image is preferably obtained with the aid of an X-ray device, in particular a C-arm X-ray device, with which relatively simple 2D projection images of an object, and in particular of a patient can be obtained from different directions. It is also possible to obtain 3D image data using the C-arm X-ray device, the C-arm being displaced some 190° about the object or patient. A series of 2D X-ray projections is taken from different directions and used to reconstruct the 3D image data set. The 3D image data of the object can however also be obtained with the aid of other imaging devices, such as a computed tomography device, an MR device or an ultrasound device, and made available for merging or superimposing with image data from projection images.

According to some variants of the invention, the digital correction information, in particular the correction angle information, is referenced to a reference plane, and in particular to the image plane of the correction image or projection image, which the user of the instrument must take full account of when correcting the guidance direction. In this respect a certain amount of imagination is also required of the user, for example how the instrument and the X-ray detector behave relative to one another. However, it is also possible to make available a correction image which has another reference plane relative to the digital correction information, for example the plane of a patient support table. In this case the digital correction information, in particular the correction angle information, is referenced to the plane of the table.

According to one embodiment of the invention, a plurality of correction images is generated in the form of projection images taken from projection directions that differ from one another, so that the instrument user can align the instrument appropriately into the desired guidance direction in space on the basis of two or more correction images and the associated digital correction information.

In a variant of the invention, the correction image is generated in the form of the projection image in such a way that the direction in which the correction image is projected is largely perpendicular to the plane through the first and second straight lines. When a C-arm X-ray device is used to record the projection image or correction image, the C-arm is aligned in such a way that the direction in which the projection image or the central ray of the X-ray beam from the X-ray source of the C-arm is projected is perpendicular to the plane through the first and second straight lines, which is then largely parallel to the plane of the X-ray receiver. In this case a single correction image obtained in said direction of projection can be sufficient for swiveling the instrument into the desired guidance direction.

According to variants of the invention, the correction diagram has at least one direction required for correction and at least one item of digital correction information referenced to said required direction, for the purpose of correcting the instrument. The correction diagram preferably has some kind of correction disk on which the directions required for correction and the items of digital correction information are associated in the direction for correction.

In an embodiment of the invention referring to the joystick display, the correction diagram has a first point indicating the instrument's current guidance direction and a second point indicating the guidance direction which the instrument is required to take. By reference to the correction diagram, the instrument has to be deviated according to the digital correction information in the correction diagram, in particular the correction angle information, in such a way that the first point, indicating the instrument's current guidance direction and virtually representing the longitudinal axis of the instrument as a point, is transferred into the second point, which indicates virtually the desired end position of the instrument's longitudinal axis and thus the required guidance direction for the instrument.

According to an embodiment of the invention, the correction diagram has unique correction direction axes which are perpendicular to one another in the plane of the correction diagram, and which are the result of selecting in the first instance a point on the first straight line and selecting a plane through said selected point, said plane being the plane of the correction diagram, so that the first straight line is perpendicular to the plane. The normal vector of the plane in the correction diagram therefore lies on the first straight line. The plane of the correction diagram and a positioning plane of the object, for example the plane of the table in the case of a patient, have a line of intersection, wherein the parallel to the line of intersection through the selected point on the first straight line and in the plane of the correction diagram produces the first correction direction axis in the plane of the correction diagram. The second correction direction axis in the plane of the correction diagram is produced by the perpendicular to the line of intersection through the selected point on the first straight line in the plane of the correction diagram. In this respect a type of two-dimensional coordinate system is obtained in the plane of the correction diagram, each correction direction axis or correction direction preferably having an associated item of digital correction information.

According to variants of the invention, at least two projection images of the object provided with the instrument are taken from mutually differing projection directions, it being possible to utilize the at least two projection images to determine the current spatial position of the tip of the instrument and/or the current spatial position of a further defined point on the instrument and/or the spatial position of the target point. By determining the current spatial position of the instrument's tip and the current spatial position of a further defined point on the instrument, it is then possible for the instrument's current guidance direction in space and the first straight line in space indicating the current guidance direction of the instrument to be computed. The second straight line is produced, as already mentioned, by the current spatial position of the tip of the instrument and the spatial position of the target point. The tip of the instrument and/or the further defined point on the instrument and/or the target point of the object can be located in the at least two projection images manually or by using a pattern recognition method. The coordinates of the identified or located spatial points are back calculated using triangulation, which is possible because for instance the projection geometries of the projection images acquired using the X-ray device, in particular the C-arm X-ray device, are known.

Moreover it is also possible to determine the current spatial position of the tip of the instrument and/or the instrument's current guidance direction in space with the aid of a position acquisition system. The position acquisition system can be optical, electromagnetic or some other suitable position acquisition system. When using an optical position acquisition system, for example, a plurality of position acquisition system markers defined on the instrument can be arranged in such a way that they can be recorded with a camera system belonging to the position acquisition system, so that both the instrument's guidance direction and the spatial position of the instrument tip can be acquired and determined using the position acquisition system.

In a variant of the invention, the target point in the object is preferably but not necessarily identified with the aid of a volume data set, for which purpose a volume data set of the object, that is, the object provided with the instrument, is recorded preoperatively or intraoperatively. Image data from the volume data set and image data from at least two projection images of the object recorded from mutually differing projection directions can then also be merged with or superimposed on one another.

According to variants of the invention, the tip of the instrument and/or the further defined point on the instrument and/or the target point of the object can be located in the volume data set or in the merged or superimposed image data from the volume data set and the at least two projection images, either manually or by using a pattern recognition method.

When a C-arm X-ray device is used, the spatial coordinates of the identified points can be determined by back projection on the basis of the known projection geometries.

BRIEF DESCRIPTION OF THE DRAWINGS

Exemplary embodiments of the invention are shown in the accompanying drawings. These show the following.

DETAILED DESCRIPTION OF THE INVENTION

Figure 1:
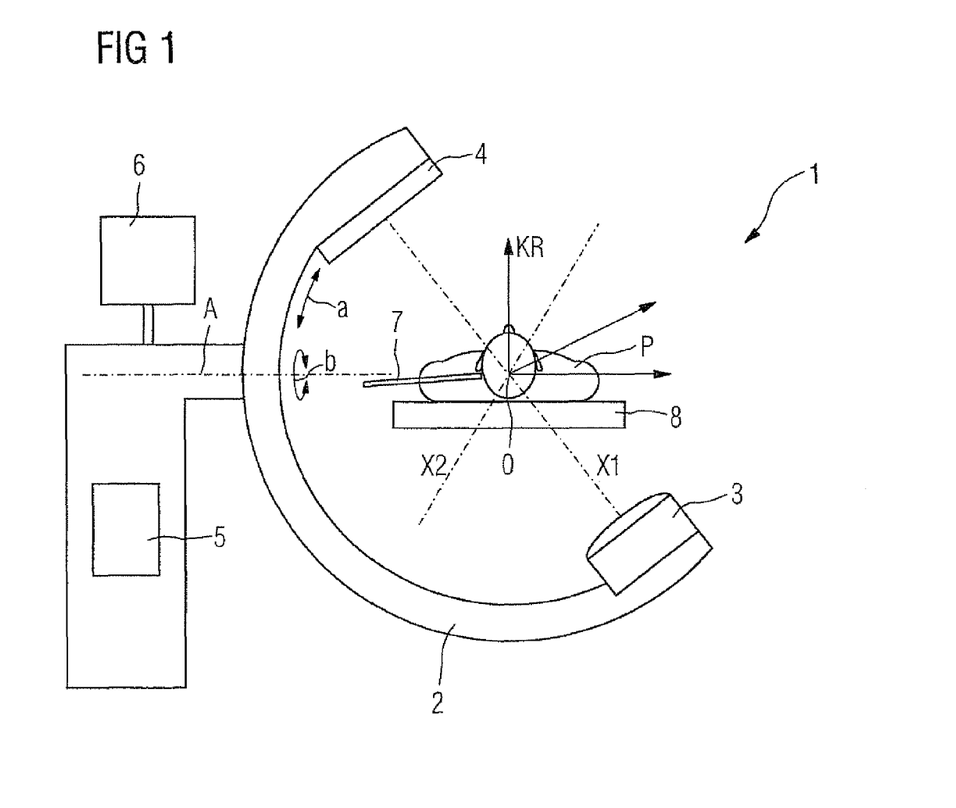
FIG. 1 A C-arm X-ray device for recording 2D projections of a patient.

FIG. 1 shows a device for making correction information available for correcting a guidance direction of an instrument when said instrument is being guided to a target location in an object, said device being provided for use in medical technology in the case of the present exemplary embodiment.

The device in the present exemplary embodiment comprises a C-arm X-ray device 1, shown as a diagram, having a C-arm 2 on which an X-ray source 3 and an X-ray receiver 4 in the form of a flat frame detector are arranged opposite one another. The C-arm 2 can be displaced in a known way in the directions of the double headed arrow a about its orbital axis O or in the directions of the double headed arrow b about its angulation axis A, in order to record X-ray projections of an object, such as a patient, from different projection directions. Furthermore the C-arm X-ray device 1 can be used to create volume data sets of an object, for which purpose the C-arm 2 is displaced about its orbital axis O through an angular range of some 190° in order to obtain for example a series of 2D X-ray recordings of the object from different projection directions. A volume data set is then reconstructed in a known way from the series of X-ray recordings, their projection geometries being known. For the purpose of acquiring, generating, providing and displaying image information, whether from 2D X-ray projections of the object or from 3D images of the object based on the generated volume data set, the C-arm X-ray device 1 has a computer 5. Image information is displayed on a viewing device 6.

The intention in the case of the present exemplary embodiment is to perform a puncture of a tissue of a patient P with the aid of the C-arm X-ray device 1 which has the computer 5, and a needle 7. For this purpose the patient P is supported on a patient table 8 as shown in the diagram in FIG. 1. In the case of the present exemplary embodiment, the puncture is performed with the needle 7 under the control of fluoroscopy, the position of the needle 7 in the patient P, in particular the position of the tip of the needle 7 relative to the tissue of the patient P needing to be punctured, being controlled with the aid of 2D projection images or transillumination images.

In the case of the present exemplary embodiment, before the actual puncture a volume data set is acquired from the patient P, in particular from the region of the patient P in which the tissue needing to be punctured is located. The volume data set can be generated preoperatively using a computed tomography device, an MR device or the C-arm X-ray device 1. However it is also possible to generate the volume data set intraoperatively, that is, during the puncture, preferably using the C-arm X-ray device 1 before or just after inserting the needle 7 into the patient P. Intraoperative generation of the volume data set with the aid of the C-arm X-ray device 1 has, provided the patient P does not move, the advantage that the volume data set does not need to be separately registered with 2D X-ray projections recorded using the C-arm X-ray device 1 during the puncture, since both the volume data and the 2D X-ray projections are acquired using the C-arm X-ray device 1 under broadly the same conditions, and are already registered with one another.

With the aid of the volume data set or a 3D image of the region of interest in the patient P based on said volume data set and able to be displayed on the viewing device 6, it is possible to establish the entry point of the needle 7 on the body of the patient P and the target point or the puncture target P3 or the target tissue in the patient P. The puncture target P3 (see FIG. 5) can be manually located in the 3D image by means of manual input via the graphical user interface of the computer 5 or by using pattern recognition methods. The position or the coordinates of the puncture target P3 in a spatial coordinate system KR can be determined by back projection.

Figure 2:
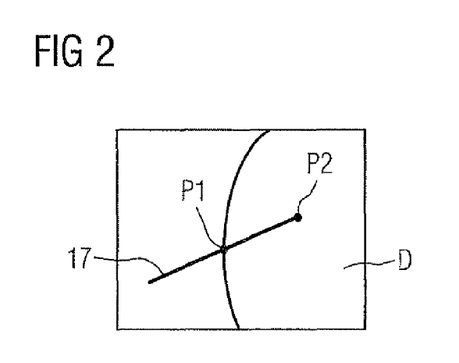
FIG. 2, 3 Two 2D projections of a patient provided with a needle, said projections having been recorded from mutually differing projection directions, FIG. 4 A display of the current guidance direction of the needle in a 3D image of the patient, FIG. 5 A display of the current guidance direction and the desired guidance direction of the needle in a 3D image of the patient, FIG. 6 A correction image in the form of a 2D projection image for correcting the guidance direction, FIG. 7 A representation of a correction diagram associated with the needle, generated in the perspective of the current guidance direction, FIG. 8 A view of the correction diagram from FIG. 7, FIG. 9 A correction image containing the correction diagram from FIG. 8 and FIG. 10 A sketch explaining the determination of the correction direction axes in the correction diagram from FIG. 8.
Figure 3:
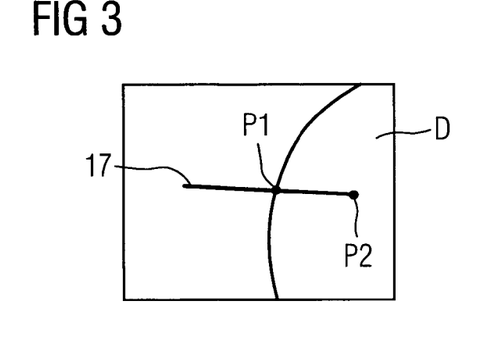
Figure 4:
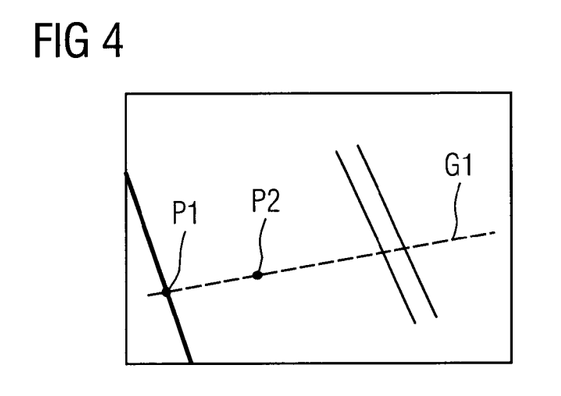

To check the position and orientation of the needle 7 once it has been inserted at the needle entry point into the patient P, after a certain time at least two X-ray projections from different projection directions are acquired with the C-arm X-ray device 1. FIG. 2 shows the 2D X-ray projection of the patient P provided with the needle 7, viewed in the projection direction X1 from FIG. 1, and FIG. 3 shows the 2D X-ray projection in the projection direction X2 from FIG. 1. In order to establish whether the current guidance direction for the needle 7 corresponds to the desired guidance direction relative to the tissue of the patient P needing to be punctured, and so that appropriate correction information can if necessary be made available to a doctor performing the puncture, the two X-ray projections shown in FIG. 2 and FIG. 3, which in each case have a representation 17 of the needle 7 and a display D of the tissue of the patient P, show the locations of the tip P2 of the needle 7 and a further characteristic point P1 on the needle 7, which in the case of the present exemplary embodiment is the needle entry point into the patient P. The points P1 and P2 are located or identified manually in the present case. However it is also possible to identify the tip P2 of the needle 7 and the point P1 on the needle 7 by using a pattern recognition method. If the points P1 and P2 in the two X-ray projection images are identified, the 3D coordinates of these points in the spatial coordinate system KR can be back calculated using triangulation if, as in the present case, the projection geometries of the projection images acquired using the C-arm X-ray device are known. Thus the computer 5 can be used to determine the coordinates of the points P2 and P1 in the spatial coordinate system KR and to set up in said spatial coordinate system KR a unique straight line G1 indicating the current guidance direction of the needle 7 in space. FIG. 4 shows a display of the straight line G1 with the points P1 and P2 in a 3D image of the patient P.

Figure 5:
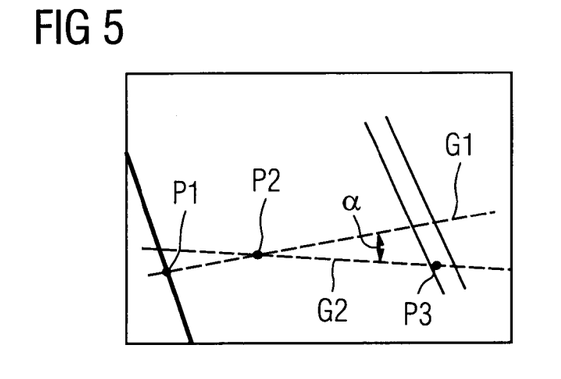

Moreover, on the basis of the spatial coordinates of the point P2 (tip of the needle 7) and the puncture target P3, it is possible to compute within the spatial coordinate system KR a straight line G2 which indicates the required guidance direction of the needle 7 and intersects the straight line G1 in the tip P2 of the needle 7. Since the straight lines G1 and G2 in space are known, it is possible to compute the angle α, between the straight lines G1 and G2, through which the needle 7 must be rotated relative to its tip P2 in order to change from the current guidance direction to the required guidance direction. FIG. 5 shows a display of the straight lines G1 and G2 in a 3D image of the patient P, in which display the puncture target P3, that is the target tissue, is also marked.

Figure 6:
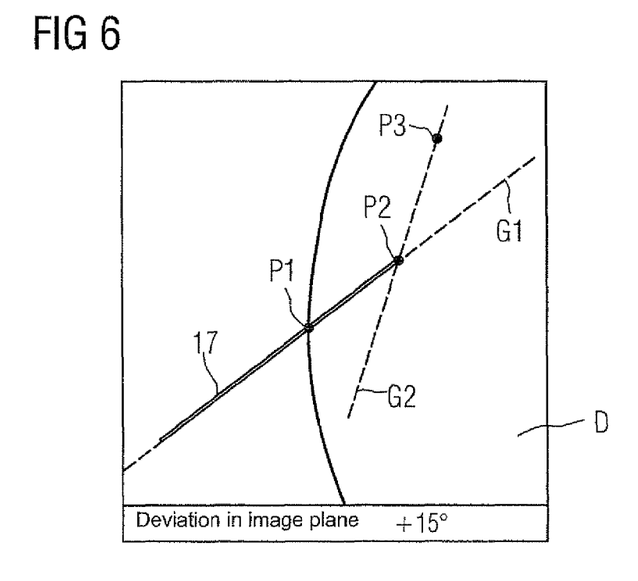

According to a first variant of the invention, and on the basis of what is known about the spatial position of the first and second straight lines G1 and G2 relative to one another, at least one correction image with at least one correction value or at least one item of digital correction information is provided for correcting the current guidance direction of the needle 7. FIG. 6 shows a correction image of this kind, said correction image being a 2D X-ray projection image onto which 3D image data can be superimposed in order to improve identification of the puncture tissue if necessary. The correction image has a representation 17 of the needle 7 and a display D of the tissue of the patient P together with a representation, corresponding to the projection direction, of the course of the straight line G1 and the course of the straight line G2. Furthermore the correction image contains the digital correction information 18, according to which the needle 7 must be rotated through the correction angle of +15° relative to the image plane about the tip P2 of the needle 7. The correction image or projection image in FIG. 6 therefore has as its reference plane the image plane of the 2D X-ray projection, which is known to the doctor maneuvering the needle 7 due to the position of the C-arm 2 relative to the patient P.

Thus in order to correct the guidance direction of the needle 7 on the basis of the correction image while taking account of the image plane as the reference plane, the doctor can accordingly deviate the needle 7 through +15° toward the correction direction entered in FIG. 6. Since the correction is specified here only in relation to a reference plane, a plurality of correction images taken from mutually differing projection directions may be necessary in order for the actual guidance direction to finally agree with the required guidance direction of the needle 7 in space. If however the projection direction of the correction image is largely perpendicular to the plane through the first and second straight lines in space (which can occur if the C-arm 2 is displaced in such a way that a central ray of an X-ray beam issuing from the X-ray source 3 is largely perpendicular to the plane through the straight lines G1 and G2), then one correction image can be sufficient for transferring the needle 7 from the current guidance direction into the required guidance direction in space.

Figure 7:
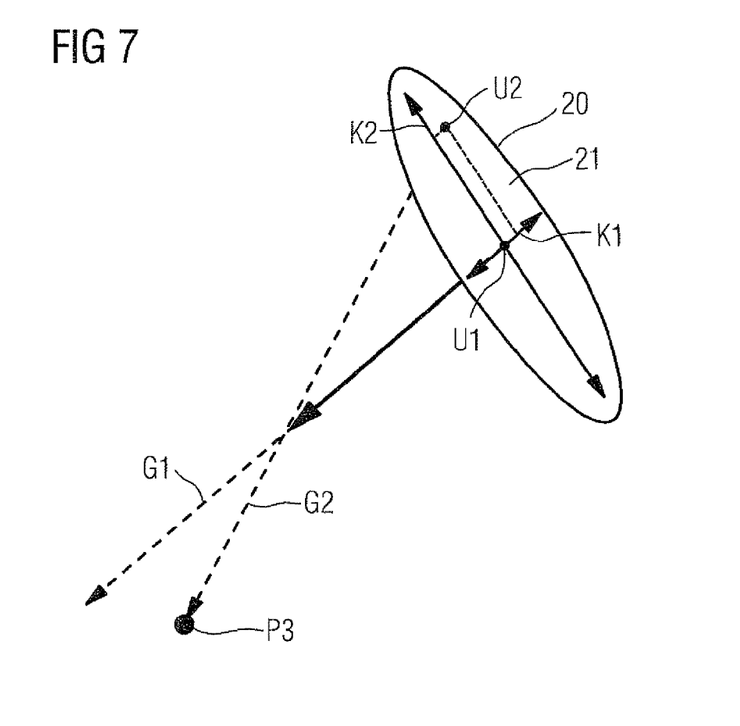
Figure 8:
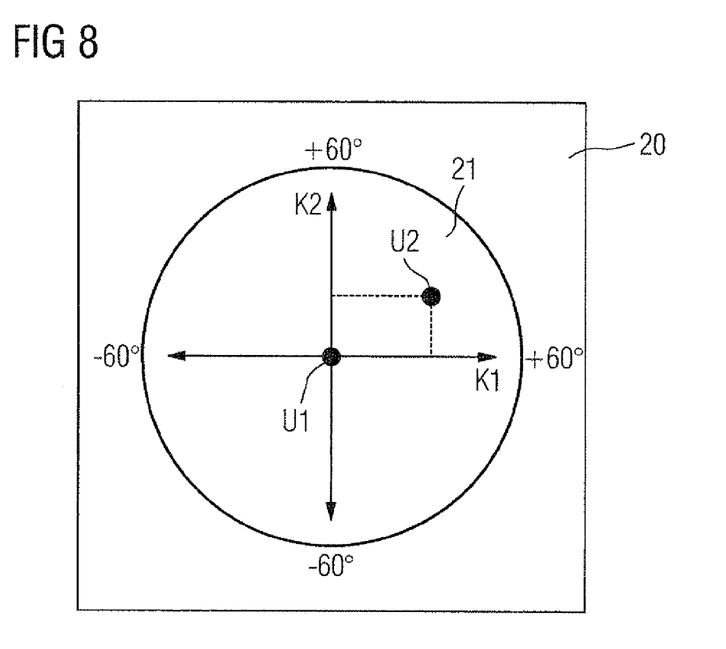
Figure 9:
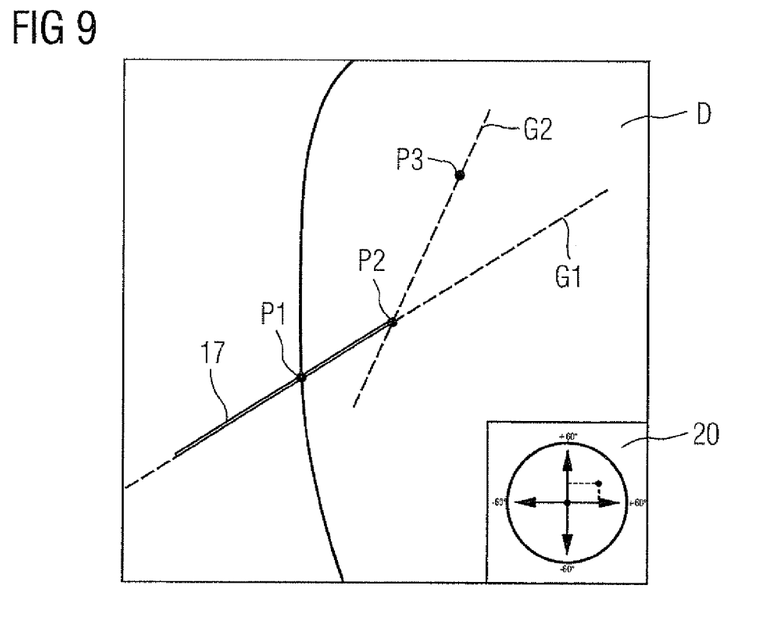

In another embodiment of the invention, the correction image can have a correction diagram 20 as shown in FIG. 7 to FIG. 9. The correction diagram 20 is located in a plane E2 in the perspective of the current guidance direction of the needle 7. This means that the current guidance direction of the needle 7, or the straight line G1, is perpendicular to the plane E2 of the correction diagram 20.

In the present exemplary embodiment, the correction diagram 20 has a correction disk 21 and two correction direction axes K1 and K2 with correction directions and with items of digital correction information referenced to the correction directions. Moreover the correction diagram 20 has a first point U1 indicating the current guidance direction of the needle 7, and a second point U2 indicating the guidance direction which the needle 7 is required to take. The correction diagram 20 is the joystick display type, which indicates to a doctor who conceptually assumes a position at the needle 7 or at the end of said needle 7 how and through which correction angle the needle 7 needs to be deviated in the direction of the correction direction axes K1 and K2 so that the needle 7 takes the required guidance direction. In this situation the correction diagram 20 can itself represent a correction image or even, as shown in FIG. 9, be displayed in a correction image such as a projection image.

Figure 10:
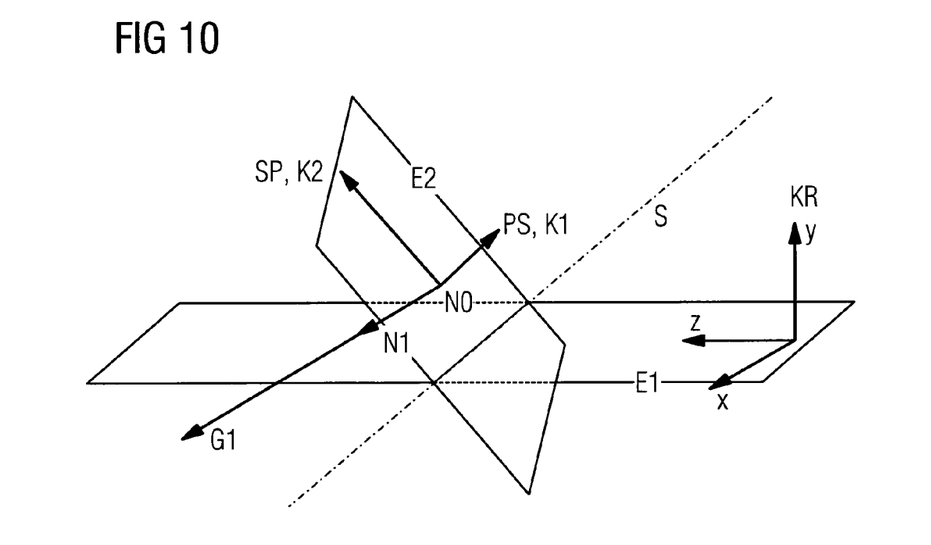

Furthermore the information on the correction directions or the correction direction axes K1 and K2 is unique, as can be seen in FIG. 10. FIG. 10 shows the straight line G1 and a plane E1, the latter being the plane of the patient table 8 on which the patient P is supported. In order to determine the correction direction axes a point N0 on the straight line G1 is selected; said point can be for example the end of the needle 7. However another point on the straight line G1 can be selected. The plane E2 is defined by the selected point P0 together with the normal vector N1 on the straight line G1, said plane E2 being the plane of the correction diagram 20. The planes E1 and E2 intersect in the line of intersection S, wherein the parallel PS to the line of intersection S through the point N0 in the plane E2 defines the first unique correction direction axis K1 in the plane of the correction diagram 20. The second unique correction direction axis K2 is produced by the perpendicular SP to the line of intersection S through the selected point N0 in the plane E2.

Finally the correction angle referenced to the correction direction axes K1 and K2 can be computed from the intercept point of the straight line G2 with the plane E2, so that a doctor who has conceptually assumed a position at the end of the needle 7 can unambiguously set the correction angle of 60° (in the present case) as specified in the correction diagram 20, and thus bring the needle 7 into the guidance direction required for said needle 7.

The invention has been described above using the example of a puncture with a needle. The invention is not however confined to the application involving punctures. On the contrary, correction information can also be inventively made available for correcting the guidance direction of other instruments, whether in the medical field or even in the field of alternative medicine.

The invention claimed is:

1. A method for correcting a guidance direction of an instrument guided to a target point in an object during an examination, comprising:
    determining a first straight line indicating a current guidance direction of the instrument based on a current position on the instrument, the first straight line defined by a characteristic point on the instrument and a point on a tip of the instrument along a longitudinal axis of the instrument;
    determining a second straight line defined by the point on the tip of the instrument and the target point in the object, indicating a desired guidance direction of the instrument, wherein the point on the tip of the instrument comprises a common point of intersection between the first and second straight lines;
    defining a reference plane from the first and second straight lines, wherein both the first and second straight lines lie in the reference plane;
    computing correction information based on a relative position of the first and the second straight line that comprises an amount that the first straight line deviates from the second straight line relative to the common point of intersection in the reference plane, the correction information representing a required change from the current guidance direction of the instrument to the desired guidance direction of the instrument in order to reach the target point in the object;
    displaying a correction image comprising a projection image of the object with representations of the instrument having its tip inserted within the object, the first straight line indicating the current guidance direction, and the second straight line indicating the desired guidance direction of the instrument, the correction image acquired from a projection direction oriented perpendicular to the reference plane defined by the first and second straight lines, wherein the correction image provides a planar view of the reference plane,
    displaying on the correction image a correction diagram represented as two axes perpendicular to one another forming a 2D coordinate plane, the 2D correction diagram comprising the correction information, wherein an origin of the axes is positioned at a first point representing the intersection of the current guidance direction and the 2D coordinate plane such that the first straight line lies on a normal vector of the 2D coordinate plane, wherein the correction diagram provides an edge view of the reference plane from a position behind the instrument with a line of sight down the longitudinal axis of the instrument such that first straight line appears as a single point, and
    wherein a second point is displayed on the 2D coordinate plane representing the intersection of the desired guidance direction and the 2D coordinate plane, to visually assist correction of the current guidance direction of the instrument to the desired guidance direction based on the correction information.

2. The method as claimed in claim 1, wherein the correction information further comprises a correction angle referenced to the common point of intersection between the first and second straight lines representing the tip of the instrument.

3. The method as claimed in claim 1, wherein the correction image further comprises a representation of the instrument and displays a course of the second straight line.

4. The method as claimed in claim 1, wherein the correction image includes a projection image of the object or a projection image of a 3D image data of the object.

5. The method as claimed in claim 1, wherein the correction information is referenced to a reference plane that is an image plane of the correction image.

6. The method as claimed in claim 1, wherein the correction diagram further comprises a correction direction representing the correction information.

7. The method as claimed in claim 1, wherein the correction diagram is displayed as a correction disk showing the correction direction axes disposed within the correction disk.

8. The method as claimed in claim 1, wherein the two axes of the correction diagram comprise a first correction direction axis and a second correction direction axis perpendicular to each other which are defined by:
    selecting a point on the first straight line,
    defining the plane of the correction diagram through the selected point so that the first straight line is perpendicular to the plane of the correction diagram,
    defining the first correction direction axis parallel to a line of intersection between a positioning plane of the object and the plane of the correction diagram through the selected point, and
    defining the second correction direction axis perpendicular to the first correction direction axis.

9. The method as claimed in claim 1, wherein at least two projection images of the object are recorded from differing projection directions for locating a current spatial position of the tip of the instrument, a current spatial position of a further defined point on the instrument, or a spatial position of the target point of the object.

10. The method as claimed in claim 9, wherein a volume data set of the object is recorded and merged with or superimposed on the at least two projection images for locating the current spatial position of the tip of the instrument, the current spatial position of the further defined point on the instrument, or the spatial position of the target point of the object.

11. The method as claimed in claim 10, wherein the locating the tip of the instrument is performed manually, or by using a pattern recognition method, or by using a position acquisition system.

* * * * *